(12) United States Patent
Dierickx

(10) Patent No.: US 7,645,808 B2
(45) Date of Patent: Jan. 12, 2010

(54) PROCESS FOR THE PREPARATION OF PROPYLENE AND ETHYLENE FROM A FISCHER-TROPSCH SYNTHESIS PRODUCT

(75) Inventor: Jan Lodewijk Maria Dierickx, Amsterdam (NL)

(73) Assignee: Shell Oil Company, Houston, TX (US)

( * ) Notice: Subject to any disclaimer, the term of this patent is extended or adjusted under 35 U.S.C. 154(b) by 6 days.

(21) Appl. No.: 11/692,738

(22) Filed: Mar. 28, 2007

(65) Prior Publication Data

US 2007/0249739 A1    Oct. 25, 2007

(30) Foreign Application Priority Data

Mar. 30, 2006    (EP) .................................. 06111957

(51) Int. Cl.
*C07C 27/00*    (2006.01)
(52) U.S. Cl. ...................................... 518/728; 518/700
(58) Field of Classification Search .................. None
See application file for complete search history.

(56) References Cited

U.S. PATENT DOCUMENTS

| 6,204,426 B1 | 3/2001 | Miller et al. ................. 585/739 |
| 6,787,022 B1 | 9/2004 | Berlowitz et al. ............. 208/18 |
| 2003/0135077 A1 | 7/2003 | O'Rear et al. ................ 585/613 |
| 2004/0267076 A1 | 12/2004 | Font Freide ................. 585/652 |

FOREIGN PATENT DOCUMENTS

| EP | 1487942 | 12/2004 |
| WO | WO0149811 | 7/2001 |
| WO | WO02070628 | 9/2002 |
| WO | WO03062352 | 7/2003 |
| WO | WO2006037805 | 4/2006 |

OTHER PUBLICATIONS

The Markets for Shell Middle Distillate Synthesis Products, Presentation of Peter J.A. Tijm, Shell International Gas Ltd., Alternative Energy '95, Vancouver, Canada, May 2-4, 1995.
P.J. Schoenmakers, J.L.M.M. Oomen, J. Blomberg, W. Genuit, G. van Velzen, J. Chromatogr. A, 892 (2000) p. 29 and further.

*Primary Examiner*—Paul A Zucker
*Assistant Examiner*—Yevegeny Valenrod

(57) ABSTRACT

A process for the preparation of propylene and ethylene comprises subjecting a gaseous mixture of a dilution gas and a paraffinic feedstock boiling in the gas oil range and having an iso paraffin to normal paraffin ratio of between 2 and 5 to a thermal conversion step.

13 Claims, No Drawings

PROCESS FOR THE PREPARATION OF PROPYLENE AND ETHYLENE FROM A FISCHER-TROPSCH SYNTHESIS PRODUCT

This application claims the benefit of European Patent Application No. 06111957.4, filed Mar. 30, 2006, which is incorporated herein by reference.

FIELD OF THE INVENTION

The invention is directed to the preparation of propylene and ethylene from a paraffinic feedstock in a steam cracker furnace.

BACKGROUND

It is well known to use the naphtha paraffin product as obtained in a Fischer-Tropsch process as steam cracker feedstock. For example in "The Markets for Shell Middle Distillate Synthesis Products", Presentation of Peter J. A. Tijm, Shell International Gas Ltd., Alternative Energy '95, Vancouver, Canada, May 2-4, 1995 on page 5, it is mentioned that SMDS naphtha, the Fischer-Tropsch derived naphtha fraction of the Shell MDS process, is used as steam cracker feedstock in for example Singapore.

WO-A-2003062352 discloses a process wherein lower olefins are prepared in a steam cracker furnace designed for petroleum naphtha starting from a Fischer-Tropsch derived gas oil.

US-A-2003/0135077 describes a process wherein a so called Fischer-Tropsch derived syncrude is blended with a sulphur containing petroleum derived naphtha and a treated crude derived fraction boiling above the naphtha boiling range. The petroleum derived naphtha, the Fischer-Tropsch syncrude and the refined heavy petroleum-derived portion are forwarded to a naphtha cracker unit for processing.

US-A-2004/0267076 describes a process wherein a Fischer-Tropsch-derived synthetic naphtha boiling in the gasoline range is subjected to a steam cracker unit for processing. A problem of the state of the art processes is that even when optimizing the propylene yield and ethylene yield the severity of the cracking operation is still relatively high resulting in a high methane yield. Methane is an unwanted by-product of the steam cracker process having only a fuel value.

SUMMARY OF THE INVENTION

The present invention provides a process for the preparation of propylene and ethylene, comprising subjecting a gaseous mixture of a dilution gas and a paraffinic feedstock boiling in the gas oil range and having an iso paraffin to normal paraffin ratio of between 2 and 5 to a thermal conversion step.

DETAILED DESCRIPTION

Applicants found that by processing a paraffinic gas oil having a relatively high iso to normal ratio a high yield to propylene in combination with a high yield to ethylene and a low yield to methane is possible. Applicants further found that higher iso to normal ratios result in a less optimal ethylene yield.

The paraffinic gas oil preferably comprises more than 90 wt % of paraffins, preferably more than 95 wt % of paraffins. Such feedstocks are obtainable by oligomerisation of lower olefins or more preferably by means of hydroisomerization/hydrocracking of normal-paraffin waxy feedstocks. Preferred normal paraffin wax feedstocks are the synthesis product of a Fischer-Tropsch process. Preferred gas oil feedstocks for the present invention are thus so-called Fischer-Tropsch derived gas oils. The paraffinic gas oil usually comprises hydrocarbons ranging from 10 to 30 carbon atoms, preferably from 11 to 28 carbon atoms, and more preferably from 12 to 25 carbon atoms.

By "Fischer-Tropsch derived" is meant that a fuel is, or derives from, a synthesis product of a Fischer-Tropsch condensation process. The term "non-Fischer-Tropsch derived" may be interpreted accordingly. A Fischer-Tropsch derived fuel may also be referred to as a GTL fuel whereby GTL stands for Gas to Liquids.

The Fischer-Tropsch reaction converts carbon monoxide and hydrogen into longer chain, usually paraffinic, hydrocarbons:

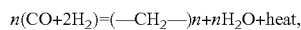

$n(CO+2H_2)=(—CH_2—)_n+nH_2O+\text{heat}$, in the presence of an appropriate catalyst and typically at elevated temperatures, for example 125 to 300° C., preferably 175 to 250° C., and/or pressures, for example 5 to 100 bar, preferably 12 to 85 bar. Hydrogen:carbon monoxide ratios other than 2:1 may be employed if desired.

The carbon monoxide and hydrogen may themselves be derived from organic or inorganic, natural or synthetic sources, typically either from coal, biomass, natural gas or from organically derived methane employing processes like for example partial oxidation or steam reforming.

Gas oil products having the desired high iso to normal ratio are suitably prepared by hydroisomerization/hydrocracking of the Fischer-Tropsch synthesis product as for example described in EP-A-1412459. Suitably the preparation involves a step wherein the feed is contacted with a dewaxing catalyst, preferably a dewaxing catalyst which is selective for isomerization of the normal paraffin compounds to iso-paraffin compounds. Preferred dewaxing catalysts comprise a molecular sieve, suitably ZSM-12, ZSM-22, ZSM-23, ZSM-48, SAPO-11. Examples of possible processes yielding the gas oil as described above are disclosed in EP-A-1487942, U.S. Pat. No. 6,204,426, EP-A-1246892 and U.S. Pat. No. 6,787,022.

Typical catalysts for the Fischer-Tropsch synthesis of paraffinic hydrocarbons comprise, as the catalytically active component, a metal from Group VIII of the periodic table, in particular ruthenium, iron, cobalt or nickel. Suitable such catalysts are described for instance in EP-A-0583836.

A Fischer-Tropsch derived gas oil preferably boils for more than 95% w/w within the typical diesel fuel ("gas oil") range, suitably within the range of from 150 to 400° C., or more suitably from 170 to 370° C., as determined by D2887-04a. Suitably, in accordance with the present invention, a Fischer-Tropsch derived gas oil will consist of at least at least 90% w/w, most preferably at least 95% w/w, of paraffinic components. The weight ratio of iso-paraffins to normal paraffins is between 2 and 5 and preferably between 3 and 4. Some naphthenic compounds and some aromatic compounds may also be present. The iso to normal ratio and the paraffin content of the blending components in the context of the present invention are measured by means of comprehensive multi-dimensional gas chromatography (GC×GC), as described in P. J. Schoenmakers, J. L. M. M. Oomen, J. Blomberg, W. Genuit, G. van Velzen, J. Chromatogr. A, 892 (2000) p. 29 and further.

A Fischer-Tropsch derived gas oil useable in the present invention will typically have a density from 0.76 to 0.79 g/cm$^3$ at 15° C.; a kinematic viscosity (ASTM D445) from 2 to 4.5, preferably from 2.5 to 4.0, more preferably from 2.9 to 3.7, centistokes at 40° C.

The gaseous mixture of a dilution gas and a paraffinic feedstock is subjected to a thermal conversion step.

Such a thermal conversion step may generally be referred to as a conversion step wherein a "cracking" reaction is performed. In such a thermal conversion step, larger molecules are broken into smaller ones. This can generally be done via a catalytic cracking method, or preferably via a thermal cracking process.

The thermal cracking process follows a homolytic mechanism, wherein carbon-carbon and carbon-hydrogen bonds break symmetrically and thus pairs of free radicals are formed. In a thermal cracking process, lighter, hydrogen-rich products are formed at the expense of heavier molecules which condense and are depleted of hydrogen at elevated temperatures and pressures.

Preferably, the thermal conversion step is executed as a steam cracking step. During a steam cracking process, a large number of chemical reactions take place, most of which are based on reactions of free radicals.

In the preferred steam cracking step, the paraffinic hydrocarbon feed boiling in the gasoil range is diluted with steam and then briefly heated in a furnace in essential absence of oxygen to a cracking temperature. Subsequently, the obtained product gas is preferably quickly quenched.

The products produced in the reaction depend on the composition of the feed, the hydrocarbon to steam ratio and on the cracking temperature and furnace residence time.

Steam cracking may result in the deposition of coke on the reactor walls, thereby reducing reactor effectiveness. Preferably some sulphur or sulphur containing compounds are present in the feed to reduce coke formation during the process. The coke formation in steam cracker furnace tubes is principally formed through two mechanisms, pyrolysis reactions and catalytic dehydrogenation reactions. The pyrolysis reactions are minimized by using low operating pressure, having high dilution gas-to-hydrocarbon ratios, on the order of 30% to 60%, and avoiding excessive tube metal temperatures and the possibility of allowing unvaporized feed into the high temperature zones. In order to withstand high tube metal temperatures, up to 1150° C., alloys containing high nickel and chromium are used, for instance 35% nickel and 25% chrome. These metals catalyze dehydrogenation reactions and therefore need to be passivated. Sulphiding is the typical solution for passivation. It is a common practice for steam cracker operators to inject coke inhibitors right after the decoking operation. That is when the tube wall metal catalyzing activities are highest. Before the hydrocarbon feedstock is fed into the furnace, DMS or DMDS is injected into the coil with steam to form a sulphide film. For a typical liquid feedstock, the sulphur content in the feedstock usually is sufficient to maintain the sulphide level during the actual steam cracking process. Sulphur may be added to the feed if there is not already enough sulphur in the feed as is typically the case for a Fischer-Tropsch derived gas oil. In this case, 20 ppmm to 100 ppmm of sulphur is added to minimize the coke and CO production. The sulphur can be added as for example a disulphide compound or by mixing the paraffinic gas oil with for example a mineral derived gas oil, a light mineral crude or a gas condensate having a certain sulphur content.

In a typical steam cracker operation, the feed first has to be heated such that it evaporates. Suitably the following steps are performed:

(a) evaporating part of the product in the presence of a dilution gas stream,
(b) further heating the gas/oil mixture to an elevated temperature and
(c) subjecting the heated gas/oil mixture to a thermal conversion step to obtain the propylene product.

The pressure and temperature in step (a) is not critical so long as the feedstock is flowable. The pressure generally ranges from between 7 and 30 bar, more preferably from 11 and 17 bar, and the temperature of feedstock is generally set from ambient to 300° C., preferably from 140° C.-300° C. Preferably step (a) is performed in the first stage preheater in the convection zone of a pyrolysis furnace. Feed rates are not critical, although it would be desirable to conduct a process at a feed rate ranging from 17 to 200 and more preferably from 25 to 50 tons of feedstock per hour. The first stage preheater in the convection section is typically a bank of tubes, wherein the contents in the tubes are heated primarily by convective heat transfer from the combustion gas exiting from the radiant section of the pyrolysis furnace. In one embodiment, as the feedstock travels through the first stage preheater, it is heated to a temperature which promotes evaporation of the paraffinic gas oil into a vapor state.

The optimal temperature at which the feedstock is heated in the first stage preheater of the convection zone will depend upon the particular feedstock composition, the pressure of the feedstock in the first stage preheater, and the performance and operation of the vapor/liquid separator. In one embodiment of the invention, the feedstock is heated in the first stage preheater to an exit temperature of at least 375° C., and more preferably to an exit temperature of at least 400° C. Each of the temperatures identified above in the first stage preheater are measured as the temperature the gas-liquid mixture attains at any point within the first stage preheater, including the exit port of the first stage preheater. Recognizing that the temperature of the feedstock inside the tubes of the first stage preheater changes over a continuum, generally rising, as the feedstock flows through the tubes up to the temperature at which it exits the first stage preheater, it is desirable to measure the temperature at the exit port of the first stage preheater from the convection zone of the furnace.

In an optional but preferred embodiment of the invention, a feed of dilution gas may be added to the feedstock in the first stage preheater at any point prior to the exit of the gas-liquid mixture from the first stage preheater. In a more preferred embodiment, dilution gas is added to the feedstock of the first stage preheater at a point external to the pyrolysis furnace for ease of maintaining and replacing equipment.

The feed of dilution gas is a stream, which is a vapor at the injection point into the first stage preheater. The dilution gas feed also assists in maintaining the flow regime of the feedstock through the tubes, whereby the tubes remain wetted, and avoids a stratified flow. Examples of dilution gases are dilution steam (saturated steam at its dewpoint), methane, ethane, nitrogen, hydrogen, natural gas, dry gas, refinery off gases, and a vaporized naphtha. Preferably, the dilution gas is dilution steam, carbon dioxide, hydrogen/carbon monoxide mixtures, also referred to as synthesis gas, a refinery off gas, a gas-to-liquids plant off-gas, more preferably a propane comprising off-gas, vaporized naphtha, or mixtures thereof.

The use of a gas-to-liquids plant off-gas, carbon dioxide or synthesis gas can be advantageously be used if the gas-to-liquids facility and step (c) of the process according the present invention, e.g. the pyrolysis furnace(s), are located close enough to benefit from a synergy. In such a situation even more preferably, use is made of the excess synthesis gas, which is contaminated with carbon dioxide and/or methane as obtained after performing the Fischer-Tropsch synthesis reaction. In the cold box of the olefin process purified synthesis gas will then be advantageously obtained, which synthesis gas can be recycled to the Fischer-Tropsch synthesis step of such a combined process. In addition to the above described dilution gasses a bleed of the hydroisomerization/hydrocracking process and/or catalytic dewaxing process can be used. The hydroisomerization/hydrocracking process and catalytic dewaxing process are the process steps in which the gas oil feed for use in the present invention is prepared.

If carbon dioxide is used as dilution gas, part of the carbon dioxide will be converted to carbon monoxide in the thermal cracking step (c). Carbon dioxide is preferably separated from the cracked effluent in the $CO_2$ absorber located upstream of or integrated with the olefin process's cracked gas compressor. The carbon dioxide is preferably recycled to step (a). The carbon monoxide and hydrogen are preferably separated from the cracked gas as a mixture of methane, carbon monoxide and hydrogen. This mixture may be advantageously recycled to the syngas manufacturing step of a gas-to-liquids process. Examples of such syngas manufacturing processes are the catalytic or non-catalytic partial oxidation, autothermal steam reforming, traditional steam reforming or convective steam reforming or combinations of said processes starting from suitably a natural gas feedstock. Other sources of syngas, e.g. from coal or from biomass may also be used.

The temperature of the dilution gas is at a minimum sufficient to maintain the stream in a gaseous state. With respect to dilution gas, it is preferably added at a temperature below the temperature of the paraffinic gas oil feedstock measured at the injection point to ensure that any water, which may be the dilution gas itself or may be present as a contaminant in some of the above referred to dilution gases, does not condense. This temperature is more preferably 25° C. below the feedstock temperature at the injection point. Typical dilution gas temperatures at the dilution gas/feedstock junction range from 140° C. to 260° C., more preferably from 150° C. to 200° C.

The pressure of dilution gas is not particularly limited, but is preferably sufficient to allow injection. Typical dilution gas pressures added to the gas oil are generally within the range of 6 to 15 bar.

It is desirable to add dilution gas into the first stage preheater in an amount up to 0.5:1 kg of gas per kg of paraffinic gas oil, preferably up to 0.3:1 kg of gas per kg of feedstock.

The gas mixture as obtained in step (a) is further increased in temperature in step (b). Preferably the gas/gas mixture has a starting temperature in step (b) of 480° C., more preferably at least 510° C., most preferably at least 535° C. The temperature of the gas/gas mixture after performing step (b) is preferably at least 730° C., more preferably at least 760° C. and most preferably between 760° C. and 815° C. Step (b) is preferably performed in the second stage preheater of a pyrolysis furnace. In the second stage preheater, the gas/gas mixture flows through tubes heated by the flue gases from the radiant section of the furnace. In the second stage preheater the mixed gas-gas mixture is fully preheated to near or just below a temperature at which substantial feedstock cracking and associated coke laydown in the preheater would occur. The heated mixture is used in step (c).

Step (c) is preferably performed in the radiant section of an olefins pyrolysis furnace where the gaseous hydrocarbons are thermally cracked to primarily propylene and ethylene and associated by-products. Further products of an olefins pyrolysis furnace include, but are not limited to, butadiene, benzene, hydrogen, and methane, and other associated olefinic, paraffinic, and aromatic products.

The pyrolysis furnace may be any type of conventional olefins pyrolysis furnace operated for production of lower molecular weight olefins, especially including a tubular gas cracking furnace. The tubes within the convection zone of the pyrolysis furnace may be arranged as a bank of tubes in parallel, or the tubes may be arranged for a single pass of the feedstock through the convection zone. At the inlet, the feedstock may be split among several single pass tubes, or may be fed to one single pass tube through which all the feedstock flows from the inlet to the outlet of the first stage preheater, and more preferably through the whole of the convection zone. Preferably, the first stage preheater is comprised of one single pass bank of tubes disposed in the convection zone of the pyrolysis furnace. In this preferred embodiment, the convection zone comprises a single pass tube having two or more banks through which the feed flows. Within each bank, the tubes may be arranged in a coil or serpentine type arrangement within one row, and each bank may have several rows of tubes.

The temperature of the product gas mixture in step (c) is preferably between 750 and 860° C. This latter temperature is sometimes referred to as the coil outlet temperature. Applicants have found that when a paraffin gas oil is processed, relatively mild operating conditions may be chosen in order to optimise the propylene yield and minimize the methane by-product yield. Preferred conditions are a coil outlet temperature of between 720 and 820° C. and more preferably between 740 and 790° C.

The temperature of the effluent of step (c), the cracked gas, is quickly reduced to a temperature of below 300° C. to terminate any unwanted reactions. Examples of reducing the temperature are by means of well known transfer line exchangers and/or by means of a quench oil fitting. Preferably the temperature is reduced to below 440° C. by means of a transferline exchanger and further reduced to below 240° C. by means of a quench oil fitting. The product gas or cracked gas is further separated into the different products as listed above by well known and described processes known to the skilled person.

EXAMPLE 1

A SPYRO® simulation was performed on a Fischer-Tropsch gas oil having an iso to normal ratio of 5.7 (Feed A), on a Fischer-Tropsch gas oil having an iso to normal ratio of 3.1 (Feed B), on a Fischer-Tropsch gas oil having an iso to normal ratio of 3.6 (Feed C) and on a standard mineral naphtha feedstock having an iso to normal ratio of 0.74 (Feed D) The simulations were performed in a simulated commercial furnace which was designed for both gas and naphtha feedstocks. The SPYRO® simulation was performed using the simulation software as referred to in the examples of U.S. Pat. No. 4,548,706.

In the simulation, the steam hydrocarbon ratio was always 0.7 kg/kg and the coil outlet temperature (COT) was varied between 760 and 820° C.

The results listed in Table 1.

TABLE 1

| | Description | Iso-normal ratio | Yields(*) at propylene maximum: | | |
| --- | --- | --- | --- | --- | --- |
| | | | Methane | Ethylene | Propylene |
| Feed A | Fischer-Tropsch gas oil | 5.7 | 10.0 | 27.5 | 19.8 |
| Feed B | Fischer-Tropsch gas oil | 3.1 | 9.8 | 28.4 | 19.7 |
| Feed C | Fischer-Tropsch gas oil | 3.6 | 10.3 | 28.2 | 19.8 |
| Feed D | Mineral derived naphtha | 0.74 | 11.4 | 24.4 | 16.1 |

(*)in % mass on feed, after hydrogenation of acetylene, methylacetylene, and propadiene

The invention claimed is:

1. A process for the preparation of propylene and ethylene, comprising subjecting a gaseous mixture of a dilution gas and a paraffinic feedstock boiling in the gas oil range and having an iso paraffin to normal paraffin ratio of between 2 and 5 to a thermal conversion step, wherein between 20 and 100 ppm of sulfur is added to the feedstock prior to performing the thermal conversion step.

2. A process according to claim 1, wherein the paraffinic feedstock comprises more than 95 wt % of paraffins.

3. A process according to claim 2, wherein the feedstock is a Fischer-Tropsch derived gas oil.

4. A process according to claim 1, wherein the iso to normal ratio of the feedstock is between 3 and 4.

5. A process according to claim 1, wherein the feedstock boils for more than 90 wt % within 150 and 400° C.

6. A process according to claim 5, wherein the feedstock has a density at 15° C. of from 0.76 to 0.79 $g/cm^3$ and a kinematic viscosity at 40° C. of from 2.5 to 4.0 cSt.

7. A process according to claim 1, wherein the dilution gas is steam.

8. A process according to claim 1, wherein the dilution gas is a mixture comprising carbon monoxide, hydrogen, carbon dioxide and methane.

9. A process according to claim 1, wherein the thermal conversion step is performed as a steam cracking step.

10. A process for the preparation of propylene and ethylene comprising subjecting a gaseous mixture of a dilution gas and a Fisher-Tropsch derived gas oil comprising more than 95 wt % paraffins and having a density at 15° C. of from 0.76 to 0.79 $g/cm^3$ and a kinematic viscosity at 40° C. of from 2.5 to 4.0 cSt, and having an iso to normal paraffin ratio of between 2 and 5 to a thermal conversion step, wherein between 20 and 100 ppm of sulfur is added to the feedstock prior to performing the thermal conversion step.

11. A process according to claim 10, wherein the dilution gas is steam.

12. A process according to claim 8, wherein the dilution gas is a mixture comprising carbon monoxide, hydrogen, carbon dioxide and methane.

13. A process according to claim 9, wherein the thermal conversion step is performed as a steam cracking step.

* * * * *